US005645809A

United States Patent [19]
Callstrom et al.

[11] Patent Number: 5,645,809
[45] Date of Patent: Jul. 8, 1997

[54] METHOD OF PRODUCING GLASSY CARBON CONTAINING METAL PARTICLES

[75] Inventors: Matthew R. Callstrom, Columbus; Richard L. McCreery, Worthington, both of Ohio

[73] Assignee: Ohio State University, Ohio

[21] Appl. No.: 529,658

[22] Filed: Sep. 18, 1995

Related U.S. Application Data

[60] Division of Ser. No. 20,198, Feb. 19, 1993, Pat. No. 5,453, 169, which is a continuation-in-part of Ser. No. 748,263, Aug. 21, 1991, abandoned.

[51] Int. Cl.[6] .................................................. C01B 31/00
[52] U.S. Cl. ..................... 423/445 R; 423/414; 204/400; 204/294; 204/291; 29/623.1; 429/40
[58] Field of Search ..................... 423/23, 138, 445 R, 423/448, 414; 29/623.1, 623.5; 429/40, 42; 204/400, 294, 291

[56] References Cited

U.S. PATENT DOCUMENTS

| 3,300,456 | 1/1967 | Hay | 260/88.2 |
| 3,332,916 | 7/1967 | Hay | 260/80 |
| 3,519,611 | 7/1970 | Hay | 260/94.1 |
| 3,767,750 | 10/1973 | Groszek et al. | 264/105 |
| 3,855,099 | 12/1974 | Matson | 204/290 R |
| 4,020,265 | 4/1977 | White | 260/80.78 |
| 4,070,333 | 1/1978 | Jabloner | 260/42.18 |
| 4,137,477 | 1/1979 | Krol et al. | 313/348 |
| 4,217,249 | 8/1980 | McVicker | 252/466 PT |
| 4,235,695 | 11/1980 | De Nora et al. | 204/268 |
| 4,271,045 | 6/1981 | Steigerwald et al. | 252/511 |
| 4,454,246 | 6/1984 | Fung | 502/213 |
| 4,518,488 | 5/1985 | Wennerberg | 208/216 R |
| 4,724,063 | 2/1988 | McIntyre et al. | 204/291 |
| 4,816,338 | 3/1989 | Terasaki et al. | 428/408 |
| 4,970,189 | 11/1990 | Tachibana | 502/183 |

FOREIGN PATENT DOCUMENTS 05 249514  9/1993  Japan .

OTHER PUBLICATIONS

Neenan et al., *Macromolecules*, 1988, vol. 21, No. 12, pp. 3525–3528 no month available.
Neenan et al., Society Symposium 3 *Advanced Materials: Insulation*, 1972, vol. 51 No. 4, Abstract no month available.
Callstrom et al., *American Chemical Society*, 1988, pp. 3528–3530 no month available.
Callstrom et al., *J. Am. Chem. Soc.*, 1990, vol. 112, pp. 4954–4956 no month available.
Callstrom et al., *American Chemical Society*, 1989, vol. 61, pp. 921–923 no month available.
Neenan, et al., *Brit. Polym. J.*, 1990, vol. 23, pp. 171–177 no month available.
Bettelheim et al., *J. Electroanal. Chem. Interfacial Electrochem.*, 1988, vol. 246, pp. 139–154 no month available.
Yasuda et al., *Journal of Inorganic and Organometallic Polymers*, vol. 1 No. 1, 1991, pp. 135–141 no month available.

Appleby, *The Electrochemistry of Carbon*, 1983, pp. 251–273 no month available.
Yeager, *The Electrochemistry of Carbon*, 1983, pp. 123–157 no month available.
Srinivasan et al., *Space Electrochemical Research and Technology*, Apr. 11–13, 1989, pp. 95–113.
Srinivasan et al., *Space Electrochemical Research and Technology*, Apr. 14–16, 1987, pp. 197–212.
Gunasingham et al., *Electroanalysis*, vol. 1, No. 3, May 1989, pp. 223–227.
Gunasingham et al., *Journal of Chromatographic Science*, vol. 27, Nov. 1989, pp. 672–675.
Tay et al., *Analyst*, vol. 113, Apr. 1988, pp. 617–620.
Itaya et al., *The Chemical Society of Japan*, 1986, pp. 571–572 no month available.
Itaya et al., *Electronal. Chem.*, 208, 1986, pp. 373–382 no month available.
Bennett et al., *Chem. Mater.* 3, 1991, pp. 490–495 no month available.
Zak et al., pp. 35–41, Preparation and Chacterization of Polyaniline Coated Platinum–doped Electrodes no date available.
Vork et al., *Synthetic Metals*, pp. C121–126, 1989 no month available.
Holdcroft et al., *Electroanal. Chem.*, 240, 1988, pp. 89–103 no month available.
Kao et al., *J. Am. Chem. Soc.*, 1984, pp. 473–476 no month available.
Shimazu et al., *Electroanal. Chem.*, 223, 1987, pp. 223–234 no month available.
Kao, *Chapter V of Thesis*, 1984, pp. 81–142 no month available.
Kost et al., *Anal. Chem.*, 1990, 62, pp. 151–157 no month available.
Bartak et al., *Anal. Chem.*, 1986, 58, pp. 2756–2761.
Kost et al., *Anal. Chem.*, Nov. 1988, 60, pp. 2379–2384.
Tsai et al., *J. Am. Chem. Soc.*, 1991, 113, pp. 1650–1652 no month available.
Gonsalves et al., *Journal of Inorganic and Organometallic Polymers*, vol. 1, No. 1, 1991, pp. 131–134 no month available.
Handy et al., *Journal of Catalysis*, 1990, 126, pp. 73–86 no month available.
Kulesza et al., *J. Electrochem. Soc.*, vol. 136, No. 3, Mar. 1989, pp. 707–713.
Wohrle et al., *Journal of Inorganic and Organometallic Polymers*, vol. 1, No. 1, 1991, pp. 115–130 no month provided.

(List continued on next page.)

*Primary Examiner*—Kathryn L. Gorgos
*Attorney, Agent, or Firm*—Fish & Richardson P.C.

[57] ABSTRACT

A method of producing glassy carbon containing metal particles includes two steps. The first step is providing a metal complexed to a molecule which can cross-link to form glassy carbon. The molecule is heated so that the molecule cross-links to form glassy carbon containing metal particles. The glassy carbon can be incorporated into an electrode for use in an electrochemical cell.

21 Claims, No Drawings

OTHER PUBLICATIONS

Utamapanya et al., *Chem. Mater.*, vol. 3, No. 1, 1991, pp. 175–181 no month provided.

Breitscheidel et al., *Chem. Mater.*, vol. 3, No. 3, 1991, pp. 559–566 no month provided.

Klabunde et al., *Chem. Mater.*, vol. 3, No. 1, 1991, pp. 30–39 no month provided.

Bagotzky et al., *Electrochimica Acta.*, vol. 29, No. 7, 1984, pp. 951–956 no month provided.

Toshima et al., *Chemistry Letters*, 1989, pp. 1769–1772 no month provided.

Weisshaar et al., *Electroanal. Chem.*, 1984, 163, pp. 395–399 no month provided.

Cowlard et al., *Journal of Materials Science 2*, 1967, pp. 507–512 no month provided.

Boag et al., *J.C.S. Dalton*, 1980, pp. 2170–2181 no month provided.

Kammereck et al., "Structure and Properties of Iron Containing Glassy Carbons", *Carbon*, 12:281–289 (1974) no month provided.

Neenan et al., "Synthesis of High Carbon Materials from Acetylenic Precursors. Preparation of Aromatic Monomers Bearing Multiple Ethynyl Groups", *J. Org. Chem.*, 53:2489–2496 (1988) no month provided.

METHOD OF PRODUCING GLASSY CARBON CONTAINING METAL PARTICLES

This is a divisional of application Ser. No. 08/020,198, filed Feb. 19, 1993, now U.S. Pat. No. 5,453,169, which is a continuation-in-part of application Ser. No. 07/748,263, filed Aug. 21, 1991, now abandoned.

BACKGROUND OF THE INVENTION

The invention relates to glassy carbon.

Glassy carbon has a unique combination of properties, including chemical and thermal inertness, hardness, impermeability to gases and liquids, and electrical conductivity. Because of these properties, glassy carbon commonly is used in carbon electrodes.

It is known to use oligomers containing acetylene groups as starting materials for making glassy carbon.

Supported metal catalysts are used in a variety of important processes, including the reforming of petroleum hydrocarbons into aromatic compounds, methanol synthesis, Fischer-Tropsch synthesis, and ethylene oxide synthesis. The largest volume user of supported metal catalysts is the automotive industry's catalytic muffler, which utilizes platinum and palladium to oxidize hydrocarbons and carbon monoxide. Dispersion of the metal catalysts on a support provides for the most efficient utilization of the metal, since small crystallites expose a large fraction of their atoms on the surface where they are available to reactants.

SUMMARY OF THE INVENTION

In general, the invention features, in one aspect, glassy carbon containing a dispersion of metal particles having an average size of less than 1 micron.

The invention features, in another aspect, an electrochemical cell in which one of the electrodes includes glassy carbon containing a dispersion of metal particles having an average particle size of less than 1 micron.

The invention features, in another aspect, an electrochemical cell in which one or both of the electrodes includes glassy carbon containing a dispersion of metal particles having a relatively uniform size distribution. By relatively uniform size distribution, it is meant that the diameter of 70% of the metal particles are less than 5 times (more preferably 3 times) the number average diameter of the particles.

The invention features, in another aspect, a method of producing glassy carbon containing metal particles. The method involves heating a metal complexed to a molecule (preferably including acetylene groups) for a sufficient period of time for the molecule to cross-link to provide glassy carbon. Preferably, cross-linking is performed at temperatures of less than 1000° C., more preferably less than 750° C., and most preferably less than 600° C. The glassy carbon can be incorporated into an electrode for an electrochemical cell.

The invention features, in another aspect, a method of producing a cross-linked carbon matrix that includes metal particles. The method includes providing a metal complexed to a molecule capable of cross-linking to form an $sp^2$-hybridized carbon matrix, and cross-linking (preferably by heating) the molecules sufficiently to form an $sp^2$-hybridized carbon matrix having microcrystalline graphite domains having average lattice dimensions of between 1 and 20 nanometers (more preferably between 2.5 and 7.5 nanometers).

The invention features, in another aspect, a method of producing a cross-linked, conductive carbon matrix. The method includes providing a metal complexed to a molecule capable of cross-linking to form a conductive $sp^2$-hybridized matrix, and cross-linking (preferably by heating) the molecules sufficiently to form an $sp^2$-hybridized carbon matrix having a conductivity of at least 0.01 s/cm (more preferably at least 0.1 s/cm).

Other aspects of the invention include using glassy carbon containing a dispersion of small metal particles to catalyze a chemical reaction (e.g., reforming, under relatively mild non-acidic conditions, without the benefit of any metal oxides; hydrogenations (including of alkynes to alkenes); dehydrogenations; isomerizations of hydrocarbons (including of alkynes to alkenes); oxidations; reductions; and pollutant removal), or to catalyze an electrochemical reaction in an electrochemical cell (e.g., a fuel cell, a cell for electrochemical synthesis, or a sensor).

The preferred metals are transition metals that have desirable catalytic or electrocatalytic properties, for example, platinum, palladium, iron, cobalt, and silver. The preferred molecules are oligomers that include diacetylene and aromatic groups. Preferably, the particles have an average size of less than 100 nanometers, more preferably less than 15 nanometers, and most preferably less than 5 nanometers. The preferred glassy carbon has a carbon content of at least 80%.

Glassy carbon is a form of $sp^2$-hybridized carbon composed of branched and entangled graphite ribbons. The structure and properties of glassy carbon are well known in the art, and are described, for example, in conventional texts such as Kinoshita, Carbon: Electrochemical and Physiochemical Properties (Wiley: New York, 1988) As is recognized by those skilled in the art, although glassy carbon is a well-known material, its properties vary somewhat based on the specific mode of preparation. For example, glassy carbons in general have good conductivity, but some forms have better conductivity than others.

The incorporation of metals on the molecular level in a carbon precursor, followed by cross-linking, results in a conductive, dimensionally stable glassy carbon matrix containing metal particles of controlled composition, size, and catalytic activity. In particular, the size of the metal particles is readily regulated by controlling the initial loading of the metal in the complex; the lower the atom percent of metal in the starting complex (preferably less than 10%, more preferably less than 5%), the smaller the resultant particle size. The small particle size makes a large surface area of metal available for participation in, for example, electrochemical or catalytic reactions. The invention thus provides a highly efficient mode of delivery for catalytic metals, most of which are very expensive. Moreover, acetylenic chemical precursors of glassy carbons are soluble in organic solvents, which makes them easy to handle and form into desired shapes, such as thin films or coatings on the outside of conventional carbon electrodes. Importantly, the amount of metal in the coating can be controlled by the dilution of the complex in the solution; the more dilute the complex, the thinner the coating formed. Additionally, the cross-linking of the acetylene precursors occur at relatively low temperatures. Also, the invention provides a convenient way to introduce more than one type of metal into glassy carbon, for example, by mixing acetylenic molecules complexed to different metals together prior to cross-linking.

Other features and advantages of the invention will be apparent from the Description of the Preferred Embodiment thereof, and from the claims.

DESCRIPTION OF THE PREFERRED EMBODIMENT

The preferred glassy carbon are prepared from aromatic acetylene molecules, typically oligomers or even larger polymers, complexed to a transition metal. Heteroatoms such as nitrogen or boron can be included in the glassy carbon as part of the aromatic ring. Other heteroatoms such as halides or silicon can be substituted for a hydrogen atom in the aromatic ring.

The acetylene groups cross link at a low temperature (e.g., less than 400° C.) to form a highly cross-linked carbon network. Further heating at temperatures typically less than 600° C. causes the microcrystalline lattice to increase in size. The transition metals can complex to either the acetylene groups, or aromatic rings, or other complexing groups included in the molecule, and are released from the complex during the cross-linking process. The metal remains trapped in the glassy carbon network as small particles of a relatively uniform size. The transition metal selected will depend on the catalytic, or electrocatalytic, properties desired, but can be, for example, platinum, palladium, titanium, ruthenium, zirconium, hafnium, iron, nickel, and silver, or combinations of these metals, if desired.

Examples of acetylenic oligomers that are suitable for complexing with transition metals to provide precursors for glassy carbon are legion, and are well-known to those skilled in the art. Representative examples of suitable complexed oligomeric precursors include those having formula 1–10, below. The oligomers may be end-capped with monofunctional acetylenes (not shown). The illustrated repeat unit of the oligomers is shown complexed to the metal; usually in the full oligomer, only a portion of the repeat units are complexed to metal atoms, depending on the metal loading into the reaction mixture that generated 1–10.

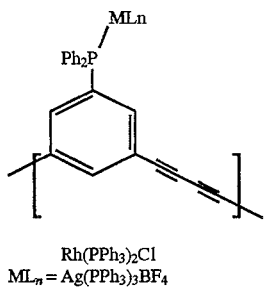

Rh(PPh$_3$)$_2$Cl
ML$_n$ = Ag(PPh$_3$)$_3$BF$_4$

1

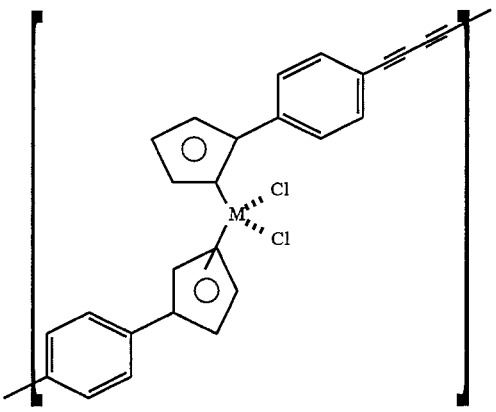

M = Tl, Zr, Hf

2

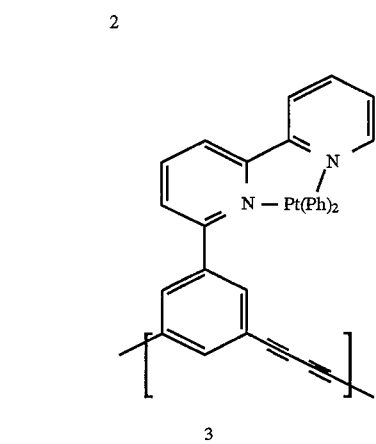

3

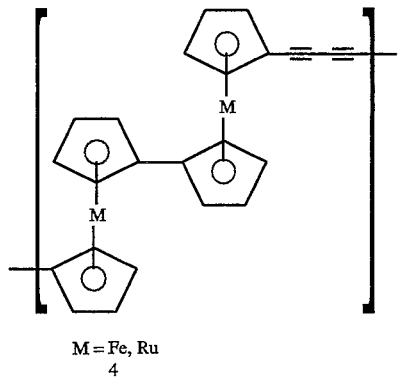

M = Fe, Ru

4

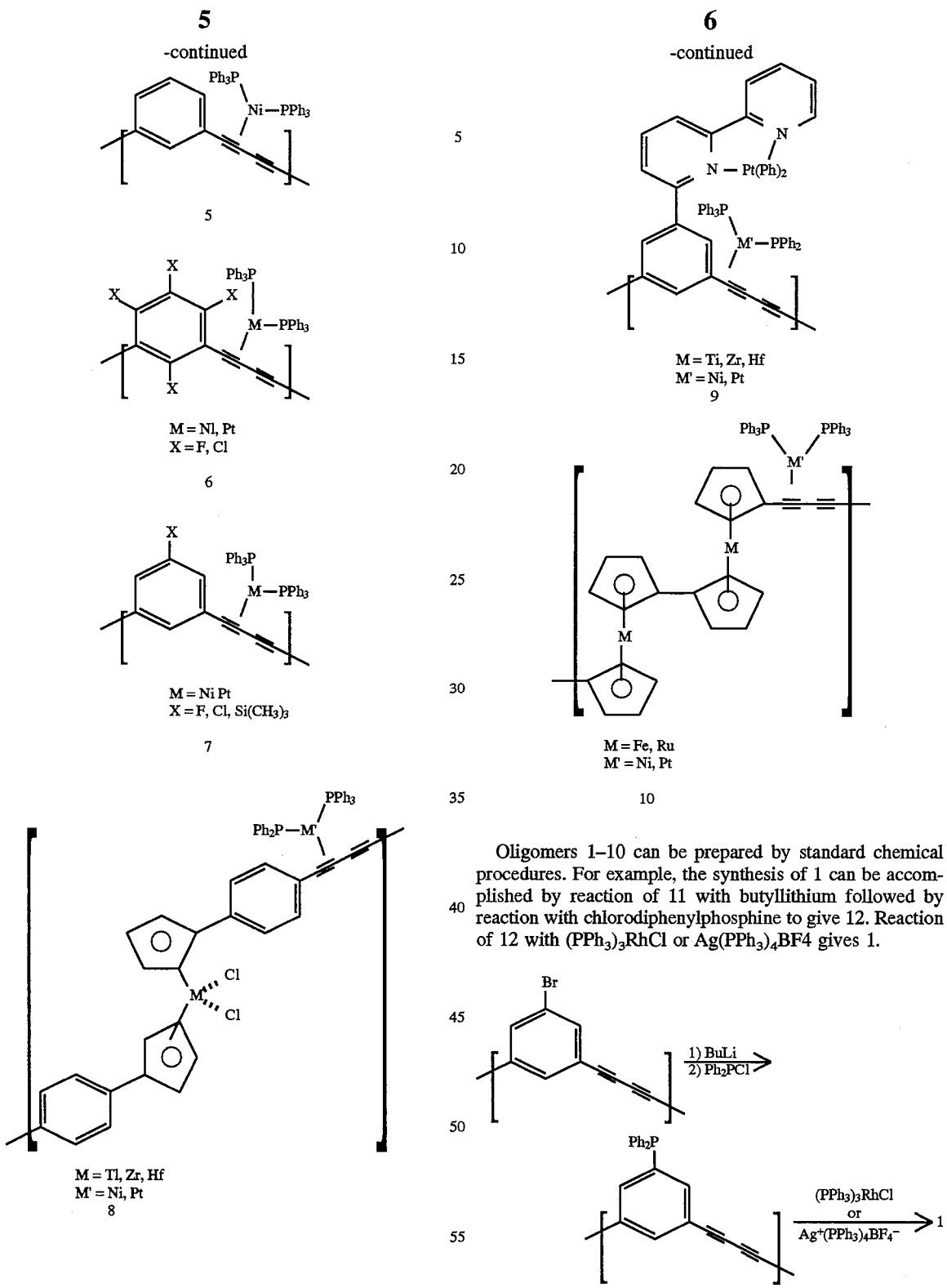

Oligomers 1–10 can be prepared by standard chemical procedures. For example, the synthesis of 1 can be accomplished by reaction of 11 with butyllithium followed by reaction with chlorodiphenylphosphine to give 12. Reaction of 12 with $(PPh_3)_3RhCl$ or $Ag(PPh_3)_4BF_4$ gives 1.

The synthesis of 2 can be accomplished by treatment of 13 with magnesium in diethyl ether, followed by reaction with cyclopentenone, followed by dehydration to give a general cyclopentadiene ligand which can be used for complexation with various metals.

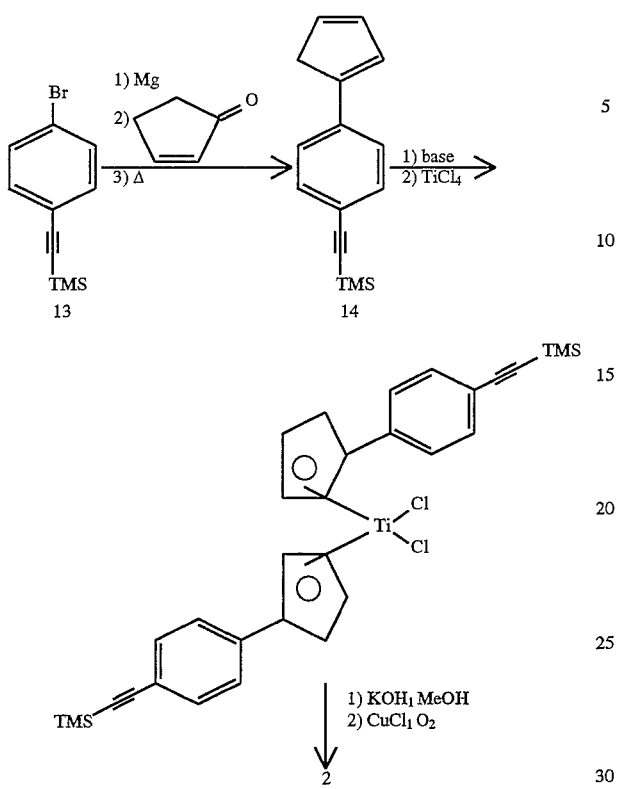

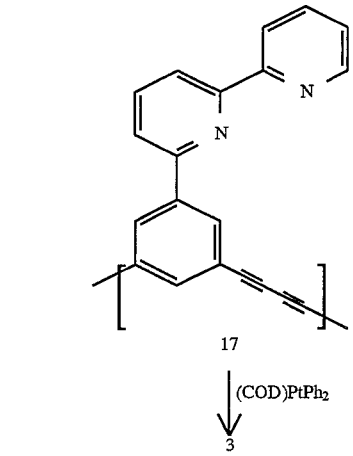

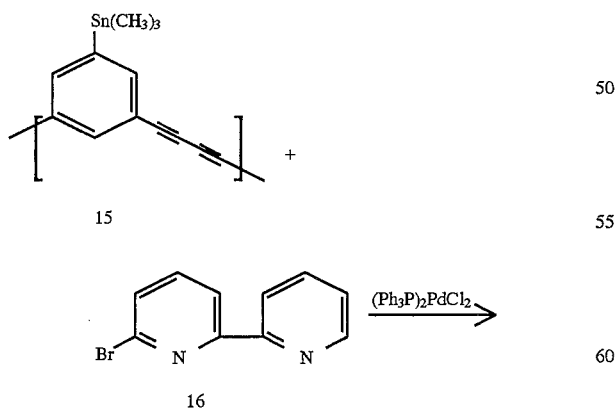

Treatment of 14 with base, such as butyllithium or sodium hydride, and reaction with TiCl$_4$ gives the diacetylene metal complex. The removal of the trimethylsilyl groups can be accomplished with catalytic potassium or sodium hydroxide in methanol or tetrahydrofuran containing water and the oligomer or polymer can be prepared by subsequent reaction with oxygen and copper chloride in o-dichlorobenzene in the presence of an amine base to give 2.

Platinum complex 3, which serves as a precursor to metal doped glassy carbon containing a bypyridyl ligand complexed with platinum, can be prepared by reaction of 15 with 16 using bis(triphenylphosphine)palladium(II) chloride as a catalyst in toluene to give 17. Reaction of 17 with (cyclooctadiene)diphenylplatinum(II) gives 3.

The complex containing iron 4 can be prepared by reaction of 1,1'-bromoacetylferrocene (18) with copper to give 19. Treatment of 19 with POCl$_3$ in dimethylformamide followed by reaction with sodium hydroxide gives 20. Reaction of 20 in the presence of copper chloride and oxygen gives 4.

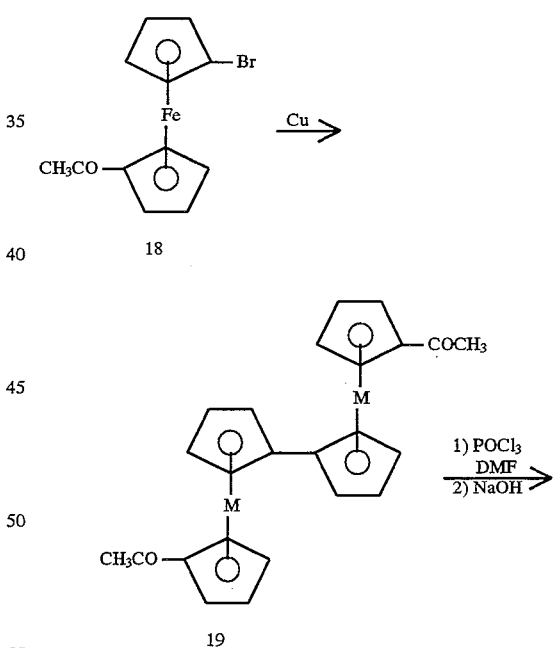

-continued

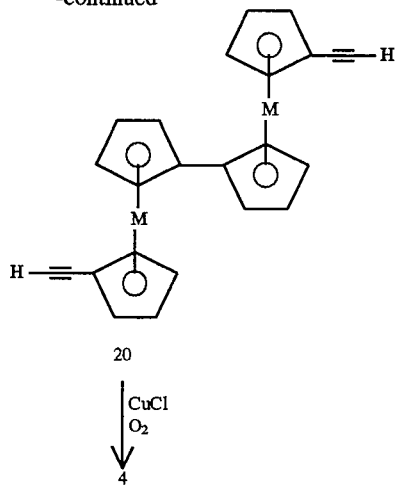

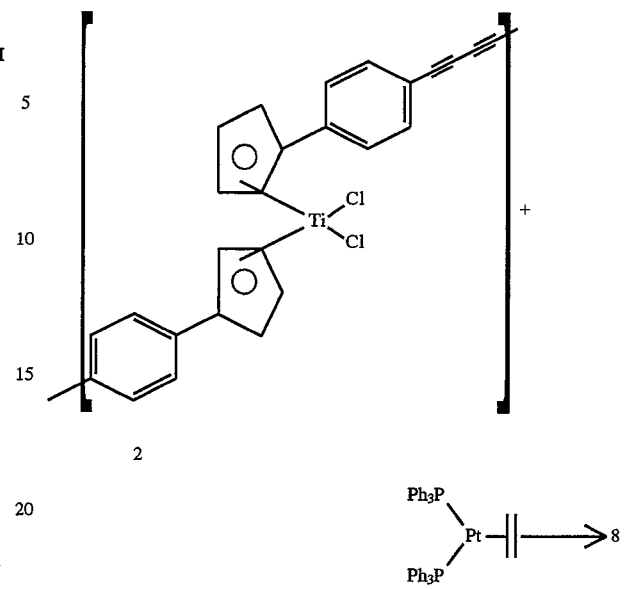

Glassy carbon precursor 5, which contains nickel, can be prepared by reaction of 21 with ethylene bis(triphenylphosphine)nickel(0).

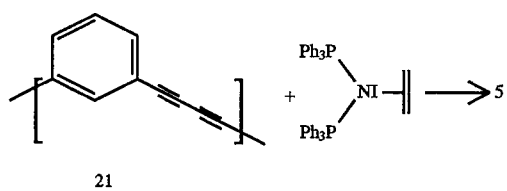

A complex that also includes fluorine (6) can be made by treatment of 22 with ethylene bis(triphenylphosphine)platinum(0) to give 6 with X=F and M=Pt. Similarly, the treatment of 23 with ethylene bis(triphenylphosphine)platinum(0) gives 7 with X=Si(CH$_3$)$_3$ and M=Pt.

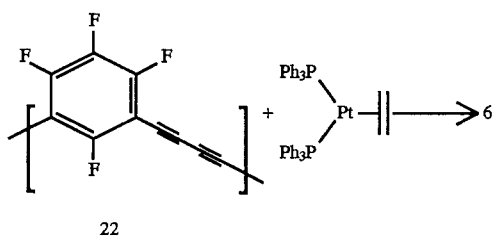

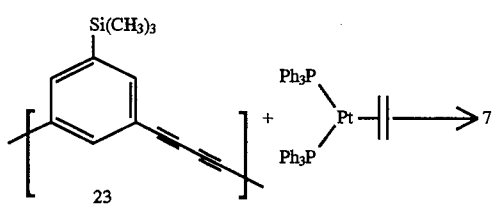

The starting complex can also include more than one metal. For example, complex 8 can be prepared by reaction of 2 with ethylene bis(triphenylphosphine)platinum(0) to give 8 with M=Ti and M'=Pt. Similarly, the treatment of 3 with ethylene bis(triphenylphosphine)nickel(0) gives 9 with M'=Ni. The treatment of 4 with M=Ru with ethylene bis(triphenylphosphine)platinum(0) gives 10 with M=Ru and M'=Pt.

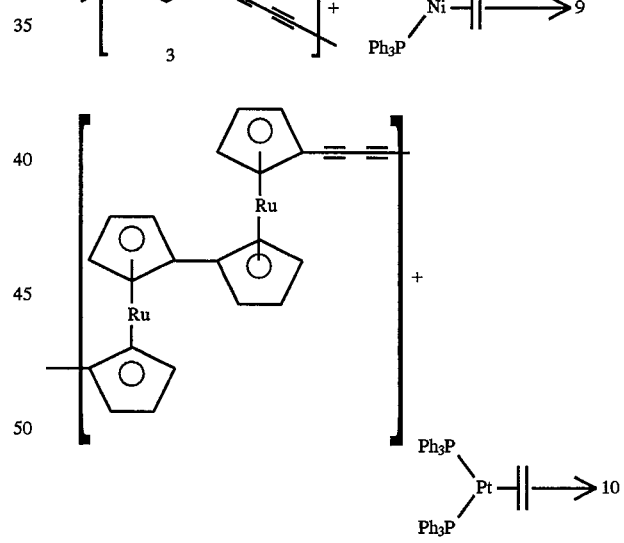

The above examples are only representative, and many other suitable complexes, and procedures for making them, are known in the art. For example, the molecular weight of the oligomers and polymers can be controlled by suitable use of end-capping groups such as phenyl acetylene, pentafluoroacetylene and the like when the molecules are prepared. The level of metal incorporated in these molecules also can be controlled by the amount of metal complex added to the acetylene molecule. In addition, glassy carbon containing a dispersion of two or more types of metal particles also can be prepared by simply mixing different metal containing oligomeric complexes prior to cross-linking and annealling.

The most preferred glassy carbons include a dispersion of platinum particles. Platinum is a catalyst for many important chemical reactions, including oxygen and hydrogen reduction. Glassy carbon including the dispersion of platinum particles can be used, for example, in oxygen/hydrogen or methanol/oxygen fuel cells. It is highly suitable for these uses because the platinum is provided efficiently in a stable matrix.

The preferred glassy carbons containing platinum particles were prepared according to the following procedures.

Ethylene bis(triphenylphosphine)platinum(0)

Ethylene bis(triphenylphosphine)platinum(0) was prepared by a three-step process.

Triphenylphosphine (1.46 g, 5.6 mmol) was dissolved in 20 mL of absolute ethanol at 65° C. When the solution was clear, 0.14 g (0.0025 mol) of potassium hydroxide in 1 mL of water and 4 mL of ethanol was added. To this, there was then added 0.5 g (1.2 mmol) of potassium tetrachloroplatinate(II), dissolved in 5 mL of water while stirring at 65° C. A pale yellow solid precipated within a few minutes of the first addition. After cooling, the compound was recovered by filtration, washed with 50 mL of warm ethanol, 20 mL of water and 12 mL of cold ethanol to give 1.17 g (78%) of product.

Carbon dioxide and oxygen were bubbled through a solution of 1.17 g (0.9 mmol) of tetrakis (triphenylphosphine)platinum(0) in 30 mL of benzene. After 45 minutes the mixture turned pale yellow and a solid precipated. The solid was recovered by filtration and washed with benzene. The crude product was dissolved in 20 mL of dichloroethane and 0.47 g (1.8 mmol) of triphenylphosphine was added. The mixture was refluxed overnight. To the mixture, 20 Ml of benzene was added and the volume was reduced by half in vacuo. White crystals were recovered by filtration, washed with benzene and ethanol to give 0.63 g (77%) of product.

A suspension of 0.61 g of [Pt(PPh$_3$)$_2$CO$_3$]·C$_6$H$_6$ in 20 mL of ethanol, under a stream of ethylene, was stirred rapidly. To this solution, 8 mL of 0.1M (0.031 g, 0.8 mmol) of sodium borohydride in ethanol was added dropwise for a period of 30 minutes. The white solid (0.442 g, 81% yield) was recovered by filtration, washed with 10 mL of ethanol, 10 mL of water, and finally with 10 mL of ethanol, and dried in vacuo.

Poly[(phenylene diacetylene) bis (triphenylphosphine)platinum(0)]

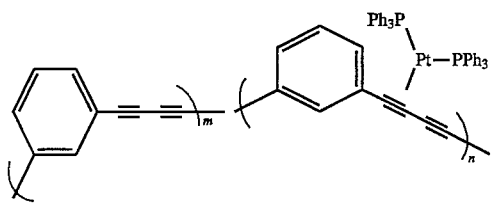

By varying the ratio of ethylenebis (triphenylphosphine) platinum(0) to poly(phenylene diacetylene), a series of complexes having the above formulae were prepared with different platinum levels. The complexes can be used to produce glassy carbon without further modification.

(a) Platinum:diyne Ratio 1:2

In 25 mL of toluene 0.3 g (0.4 mmol) of ethylene bis(triphenylphosphine)-platinum(0) was dissolved with 0.1 g (0.8 mmol of phenyldiyne unit) of poly(phenylene diacetylene). The mixture was heated to 65° C. for 6 hours. After 2 hours, the solution turned from pale yellow to dark brown. This solution was poured into 250 mL of petroleum ether and a solid precipitated. The oligomer (0.270 g, 69%) was recovered by filtration and washed with ethanol.

(b) Platinum:diyne Ratio 1:4

In 25 mL of toluene 0.15 g (0.2 mmol) of ethylene bis(triphenylphosphine) platinum(0) was dissolved with 0.1 g (0.8 mmol of phenyldiyne unit) of poly(phenylene diacetylene). The mixture was heated to 65° C. for 6 hours. After 2 hours, the solution turned from pale yellow to dark brown. This solution was poured into 250 mL of petroleum ether and a solid precipitated. The oligomer (0.10 g, 60%) was recovered by filtration and washed with ethanol.

(c) Platinum:diyne Ratio 1:6

In 25 mL of toluene 0.1 g (0.13 mmol) of ethylene bis(triphenylphosphine)-platinum(0) was dissolved with 0.1 g (0.8 mmol of phenyldiyne unit) of poly(phenylene diacetylene). The mixture was heated to 65° C. for 6 hours. After 2 hours, the solution turned from pale yellow to dark brown. This solution was poured into 250 mL of petroleum ether and a solid precipitated. The oligomer (0.05 g, 60%) was recovered by filtration and washed with ethanol.

Tetrakis[bis[1-(3-phenylbutadiynyl)phenyl] phenylphosphine]platinum(0)

An alternative starting complex, tetrakis[bis[1-(3-phenylbutadiynyl)phenyl]phenylphosphine]platinum(0), which has the below formula, was prepared in two steps.

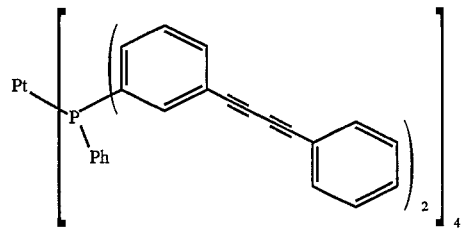

First, to 3 g (10 mmol) of (1-bromo-3-phenylbutadiynyl) benzene dissolved in 65 mL of tetrahydrofuran, 7 mL (11 mmol) of n-butyllithium (1.6M in hexanes) was added slowly to the solution at −78° C. The solution turned dark brown after 5 minutes. The solution was stirred at −78° C. for 2 hours and then 0.71 mL (5.3 mmol) of dichlorophenylphosphine was added slowly. The solution immediately turned yellow. The solution was allowed to warm to room temperature and to stir overnight. The reaction was quenched with a saturated solution of ammonium chloride, the solids removed by decantation, and the organic layer was washed with ammonium chloride solutions and dried with anhydrous magnesium sulfate. After filtration of the solid, the solvent was removed in vacuo, and the yellow residue was purified by column chromatography on silica gel (20% CH$_2$Cl$_2$ in hexanes) to give 0.7 g (20%) of light white crystals.

The bis[1-(3-phenylbutadiyne)phenyl]phenylphosphine (0.47 g, 0.09 mmol) was dissolved in the minimum amount of benzene (4 mL) and then diluted in 10 mL of ethanol. The solution was heated to 65° C. and when the solution turned clear, 0.5 mL of a solution of 0.21 g (0.004 mol) of potassium hydroxide in 1 mL of water and 4 mL of ethanol was added. To this, there was then added dropwise, 0.0832 g (0.2 mmol) of potassium tetrachloroplatinate(II) dissolved in 5 mL of water, while stirring at 65° C. After the first drops, the solution became cloudy, and a yellow solid precipitated. The solid (0.129 g, 51%) was recovered by filtration and washed with 20 mL of warm ethanol, 10 mL of water and 15 mL of ethanol.

Glassy Carbon

The acetylenic complexes described above can be converted to glassy carbon at relatively low temperatures. The initial heating causes the acetylene groups to cross-link, forming a highly cross-linked carbon matrix. The cross-linking can be carried out at temperatures below 500° C. (e.g., 350° C.). Upon further heating, the cross-linked matrix anneals, to provide glassy carbon. Annealization typically requires heating at a higher temperature (e.g., 550° C.–700° C.) than the initial cross-linking. Both steps can be carried out simultaneously by simply heating at the higher temperature.

Preferably, the glassy carbons should have a conductivity greater than 0.01 s/cm, more preferably greater than 0.1 s/cm, and most preferably greater than 0.7 s/cm. The microcrystalline graphite dimensions, as determined by conventional Raman spectroscopy and X-ray powder diffraction techniques, are between 1 and 20 nanometers, more preferably greater than 2 nanometers, and most preferably between 2.5 and 7.5 nanometers. The glassy carbon electrode should function as a practical electrode. Preferably, in cyclic voltametry of ferris ferrocyanide, the oxidation-reduction separation should be $\Delta Ep < 200$ mV, more preferably $< 150$ mV, and most preferably $< 100$ mV.

The conversion of the platinum-complex precursors to glassy carbon was performed by alternative procedures, one which resulted in pellets of glassy carbon; the other which resulted in a film on a pre-existing glassy carbon disc and on carbon felt.

a) Glassy Carbon Pellets

Glassy carbon pellets were made in two steps. Approximately, 150 mg of a precursor were submitted to a pressure of 3500 psi at a temperature of 350° C. for 2 hours in a 1 cm diameter steel die. A Carver laboratory press model C was used. The sample was allowed to cool slowly. At the end of this period, a 1 cm diameter black disc of cross-linked carbon solid was obtained. The pellets were then sealed in vacuo in a quartz tube and heated to 600° C. at a rate of 1° C./min for a total period of 15 hours in a Thermolyne type 6000 furnace, and then allowed to cool at a rate of 1° C./min to room temperature.

b) Glassy Carbon Films

A toluene solution of a precursor was spin-coated (Headway Research, PWM101 model) on an Atomergic V25 glassy carbon disc. The solvent was evaporated and the disc was sealed in vacuo and thermally treated to 600° C. under the same conditions as that for the pellets. A similar procedure can be used to coat a variety of materials, including carbon felt, carbon filters, other metals, silica, and alumina. Importantly, this provides the uses with the ability to take a variety of backings and turn them into, e.g., a platinum electrode, by simple coating procedures.

Raman analysis confirms the glassy carbon microcrystalline structure of these carbon solids exhibiting bands at approximately 1580 cm$^{-1}$ and 1360 cm$^{-1}$, consistent with the formation of an sp$^2$-hybridized carbon lattice. The x-ray photoelectron spectroscopic analyses and microprobe analysis confirmed the incorporation of approximately 0.5 to 1 atom % of platinum(0) in glassy carbon.

The size of platinum particles can be determined by standard transmission microscopic analysis. For example, a thin film of the glassy carbon containing dispersed platinum particles was prepared by evaporation of a glassy carbon precursor onto a sodium chloride disc to give a 2–3 micron thick coating. The disc was then heated to 600° C. to provide a film of glassy carbon. The film was then lifted from the disc, and a transmission electron micrograph of the edge of the film is taken, and the diameters of the particles (or clusters) are recorded, and a mean obtained. The average platinum particle size in the glassy carbons obtained from the previously described precursors in the range of 1.4 to 2.1 nanometers.

H$^+$ Reduction (a) The glassy carbons of the invention are useful in a wide variety of catalytic and electrochemical applications. For example, glassy carbon containing dispersed platinum particles, when used in place of platinum in a platinum disc electrode and studied for its effect on the reduction of H$^+$ to H$_2$, exhibited a performance close to that of a pure platinum disc.

(b) An electrode was also prepared by applying 5 drops of a saturated solution of a 1:2 platinum:diyne ratio of poly[(phenylenediacetylene) bis(tri-phenylphosphine) platinum (0)] in toluene to each side of a carbon felt electrode, which consisted of a matrix of carbon fibers. The electrode was heated under vacuum to 600° C. (1° C./min), and cured at 600° C. for 6 hours to provide the glassy carbon. The resulting electrode was used in place of a standard platinum disc electrode. Voltrametry was taken in a 1M H$_2$SO$_4$ solution at different scan rates in the range of 0.2 V to –0.6 V versus a conventional Ag/AgCl reference electrode.

(c) The activity of the platinum dispersed in glassy carbon was compared to a polycrystalline platinum electrode for H$^+$ reduction over time at constant potential. A 1 atom % platinum in glassy carbon thin film on conventional glassy carbon was held at constant potential of –0.044 V vs NHE in 1 molar HClO$_4$ solution for a period of 60 min. The current density of the 1 atom % platinum containing glassy carbon exhibited a higher current density than did a polycrystalline platinum electrode mounted in glass at times greater than 10 min.

O$_2$ Reduction

The activity of the platinum dispersed in glassy carbon was compared to a polycrystalline platinum electrode and a conventional glassy carbon electrode for oxygen reduction. A 1 atom % platinum in glassy carbon thin film on conventional glassy carbon was exposed to oxygen in 1M HClO$_4$ buffer and scanned at 50 mV/sec from 1.0 to –0.5 V vs SSCE. The current density and potential for O$_2$ reduction with the platinum in glassy carbon electrode exhibited a performance close to that of a pure platinum disc. In the case of the carbon felt electrode including a thin coating of glassy carbon containing platinum particles, the porosity, stability, and catalytic efficiency of the electrode should be very useful for electrochemical applications.

Reforming

The ability of Pt-DGC to accomplish the aromatization of hexane derivatives was investigated (Table 1). The Pt-DGC catalyst was prepared by the thermal treatment (600° C.) of poly[(phenylene monoacetylene)bis(triphenylphosphine) platinum (0)]. The preparation of this material is described further below. The ratio of platinum to diacetylene unit was 1:2. The x-ray photoelectron spectroscopic analysis of the Pt-DGC indicated that the material contained –0.5 atom % platinum. The heterogeneous catalytic reactions were carried out at 515° C. in a constant flow fixed-bed reactor. The products were identified via gas chromatography by a comparison of retention times with authentic samples. The aromatization of 1,5-hexadiene with Pt-DGC was studied in the presence of helium and hydrogen mixtures. In a typical experiment, the platinum doped oligomer was cast as a thin film in the reactor tube and heated to 600° C. under dynamic vacuum conditions (0.005 torr) to give a Pt-DGC coating containing ~0.5 atom % platinum.

TABLE 1

The Aromatization of 1,5-Hexadiene and n-Hexane with Platinum Doped Glassy Carbon Containing 0.5 Atom % Platinum

| Trial Number | Temperature (°C.) | Carrier Gas | Starting Material | Mass % Benzene |
|---|---|---|---|---|
| 1 | 515 | He:H$_2$(80:20) | 1,5-hexadiene | 15.3% |
| 2 | 515 | He:H$_2$(80:20) | 1,5-hexadiene | 4.1% |
| 3 | 515 | He:H$_2$(80:20) | 1,5-hexadiene | 3.6% |
| 4 | 515 | He:H$_2$(80:20) | 1,5-hexadiene | 3.2% |
| 5 | 515 | H$_2$(100) | n-hexane | 2–3% |

The catalyst was activated by heating in situ to 500° C. for 5–10 h under flowing hydrogen (20 ml/min). Helium was then used to bring the total flow to 60 ml/min, and 1,5-hexadiene vapor was passed through the catalyst at a rate of 0.1 ml/min. Benzene was identified by comparison of the G.C. retention times with an authentic sample. The overall conversion to benzene occurred in a 15% yield by G.C. (Table 1). The catalyst was regenerated with flowing hydrogen at 515° C. for 18th prior to this reaction. Trial 5 illustrates the ability of Pt-DGC to produce benzene from n-hexane. Various ratios of hydrogen and helium were used to maximize the efficiency of the 1,5-hexadiene reactions. The presence of hydrogen is necessary for aromatization reactions mainly to maintain catalyst activity. However, hydrogen can also affect the direction of the reactions by increasing the degree of hydrogenation. The goal is to maintain catalyst activity while maximizing the catalyst's selectivity to form benzene. The highest selectivity for the conversion of 1,5-hexadiene to benzene was obtained using an 80:20 mixture of helium and hydrogen (Table 2).

TABLE 2

Product Distribution in the Aromatization of 1,5-Hexadiene and n-Hexane.

| Trial | 1,5-hexadiene | benzene | Conjugated Hexadienes | Hexenes | Hexanes |
|---|---|---|---|---|---|
| 1 | 87.1 | 12.3 | 0.3 | 0.1 | 0.2 |
| 2 | 92.3 | 4.1 | 1.2 | 1.6 | 0.8 |
| 3 | 93.3 | 3.6 | 2.3 | 0.8 | — |
| 4 | 92.8 | 3.2 | 3.1 | 0.8 | 0.1 |
| 5 | — | 1.8 | 0.8 | — | 95.0 |

As illustrated in Table 2, the selectivity of the catalyst suffered upon repetitive use. (Only the major products are identified.) Specifically, the isomerization of 1,5-hexadiene to the conjugated 1,3-and 2,4-hexadiene isomers became a major reaction pathway as the catalyst activity diminished. As Trial 4 illustrates, this attempt to regenerate the catalyst with flowing hydrogen at 515° C. failed to produce the result obtained in Trial 1. The selectivity of the reaction also failed to improve upon catalyst regeneration. It is significant, however, that catalyst activity stabilizes at the new level of 2–4% conversion to benzene. This stability is significant because many applications utilize a recycling reactor to generate a greater yield of the desired product. In these cases, the catalyst stability is more important than initial reactivity.

Synthesis of Poly(phenylene Monoacetylene) Oligomers

Poly(phenylene monoacetylene) oligomers were synthesized as illustrated below:

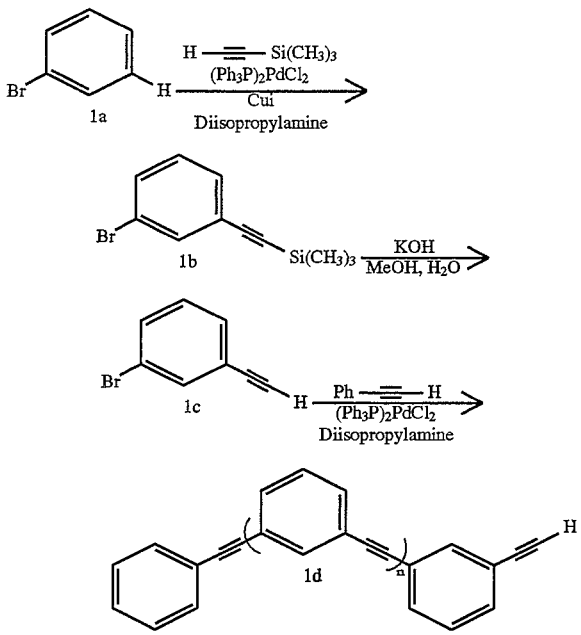

Compound 1a was smoothly coupled with one equivalent of trimethylsilylacetylene using palladium and copper catalysis in diisopropylamine (see Takahashi et al., *Synthesis*, 1980, 617–30; Austin et al., *J. Org. Chem.*, 1981, 46, 2280–86). The trimethylsilyl ethynyl derivative (1b) was deprotected with potassium hydroxide in aqueous methanol to give the free ethynyl derivative (1c). Polymerization of the ethynyl derivative was accomplished using bis(triphenylphosphine) palladium (II) chloride in diisopropylamine at 65° C. A ratio of 1c to ethenylbenzene of 3:1 was used to control the molecular weight and tractability of the oligomers. The homogeneous diisopropylamine solution was concentrated in vacuo, and the solid residue was dissolved in benzene. The oligomers were precipitated by the addition of an equal volume of 5% hydrochloric acid in methanol to the benzene solution, and collected via centrifugation. The oligomers could then be molded into disks, via thermal and pressure treatment (330° C., 6800 bars), or cast as thin films on commercial glassy carbon. Thermal treatment to 600° C. under a dynamic or static vacuum (0.05 torr) produced glassy carbon.

Poly(phenylene acetylene) was doped with platinum via the reaction of bis(triphenylphospine)platinum (II) ethylene with 1d:

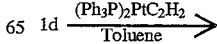

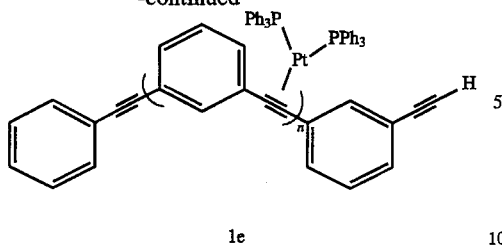

1e

Gram quantities of Pt-DGC were synthesized from the monacetylene oligomer 1d. In addition to catalyzing the reformation reaction, this material will be used in heterogenous organic catalysis reactions such as carbon-hydrogen bond activation and hydrogenation of ethynyl, vinyl, and nitrile, carbonyl, and nitro moieties.

(a) Synthesis of 1-bromo-3-trimethylsilylethynylbenzene (1b)

To a solution of m-bromoiodobenzene (25.0 g, 881.1 mmol) in diisopropylamine (500 ml), there were added bis(triphenylphosphine)palladium dichloride (1.24 g, 1.80 mmol) and copper (I) iodide (1.24 g, 2.03 mmol). The solution was degassed via a rapid stream of argon, and trimethylsilylacetylene (9.51 g, 97.0 mmol) was added over a period of 15 min. The reaction mixture was stirred at room temperature until G.C. analysis indicated the disappearance of starting material (2 h). The reaction mixture was cooled to room temperature and filtered to remove salts. The filtrate was concentrated in vacuo, and the oily residue was taken up in dichloromethane. The solution was washed with an aqueous 5% HCl solution (2×200 ml), water (2×200 ml) and brine (1×200 ml). The combined organic layers were dried (MgSO$_4$) and the solvent removed in vacuo yielding the crude product as a yellow oil. The liquid chromatographed from silica gel in pentane. Elution with pentane gave the product (1b) (20.59 g, 91%) as a clear liquid: bp 81°–82° C., $^1$H NMR (200 MHz, CDCl$_3$) c 0.30 (s), 7.23(m).

(b) Synthesis of 1-bromo-3-ethenylbenzene (1c)

To a solution of 1-bromo-3-trimethylsilylethynylbenzene (20.5 g, 81.0 mmol) in degassed methanol (500 ml), there was added potassium hydroxide (31 mg, 0.55 mmol) in water (1 ml). The solution was stirred at room temperature until G.C. analysis indicated the reaction was complete (5.0 h). The reaction mixture was diluted with an equal volume of water, and extracted with n-pentane (5×500 ml). The combined organic layers were dried (MgSO$_4$) and the solvent removed under reduced pressure to yield a yellow liquid. The liquid was distilled via bulb-to-bulb vacuum distillation to yield the product (1c) (13.0 g, 90%) as a clear liquid: bp 40° CC/1 torr; $^1$H NMR (200 MHz, CDCl$_3$) c3.35(s), 7.23(t), 7.40(m), 7.65(t).

(c) Synthesis of Poly(phenylene Acetylene) (1d)

To a degassed solution of diisopropylamine (200 ml), there was added bis(triphenylphosphine) palladium dichloride (0.773 g, 1.102 mmol). To this green heterogeneous solution, there were added 1c (10.0 g, 55.1 mmol) and phenylacetylene (1.2 g, 12.0 mmol). The reaction mixture was heated to reflux until G.C. analysis indicated the disappearance of starting materials (12 h). The reaction mixture was filtered to remove salts and the filtrate concentrated in vacuo yielding the product as an oily residue. The solid residue was taken up in benzene and poured into an equal volume of 5% HCl in methanol to induce precipitation. The oligomer was collected via centrifugation yielding 1d as a light yellow powder (9.70 g, 88.0%).

Hydrogenation

Tetrakis(triphenylphosphine) palladium (I) was mixed with polyphenylenediacetylene (IV) to yield palladium-doped oligomer V:

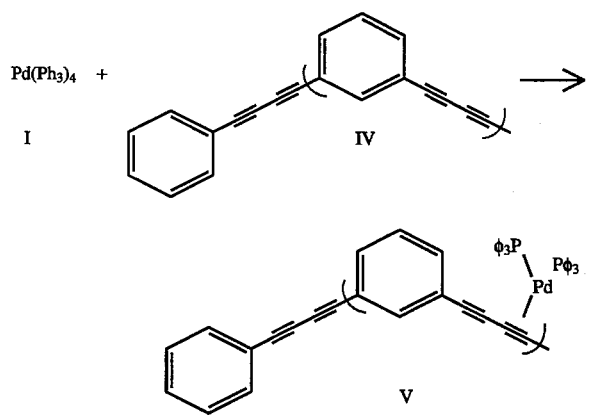

Oligomer V was converted to palladium-doped glassy carbon (Pd-DGC), and was used to catalyze the selective hydrogenation of phenylacetylene (VI) to styrene (VII):

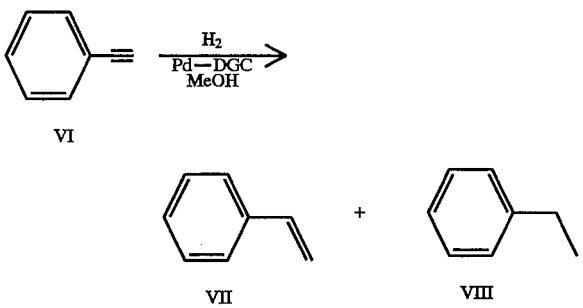

Experimental

All glassware was oven-dried or flame-dried prior to use. All solvents were used as purchased. Reaction mixtures were degassed with a bubbling stream of Ar for 10 min. Melting points were obtained with a Thomas-Hoover capillary melting point apparatus. Hydrogenation gas chromatograms were performed on a Hewlett-Packard 5790 instrument. The $^1$H nuclear magnetic resonance spectra were recorded on a Bruker AC 200 MHz to 250 MHz instrument. The $^{31}$p nuclear magnetic resonance spectra were recorded on a Bruker AC 250 MHz instrument. Infrared spectra were performed with a Perkin-Elmer 1600 Ft-IR. The x-ray photoelectron spectra were collected with a Physical Electronics 550 ESCA/AUGER spectrometer. A monochromatic X-ray source using an Mg anode (Mg kα, 300 Watts, 15 kV) was employed as the primary excitation source.

Polyphenylenediacetylene (IV, 0.15 g) was physically mixed with 0.82 g of tetrakis (triphenylphosphine) palladium (I) until the mixture was homogenous, to yield V. The Pd-doped oligomer V (200 mg) was placed in a die and heated to 300° C. under 12,000 PSI for one hour. The resulting pellet was cured at 600° C./6 h under 0.005 mm Hg. The pellet was crushed and powdered in a Wig-L-Bug mortar and pestle container.

To a 500 mL Parr bottle, there was added powdered Pd-DGC (116 mg, Pd: 6.1 mg, 0.057 mmol) and degassed methanol (200 mL). Phenylacetylene (0.64 mL, 57.2 mmol)

was added. The container was evacuated via vacuum aspirator and flushed with three cycles of $H_2$. The reaction vessel was filled with $H_2$ (45 PSI) and monitored periodically by gas chromatography (GC). The bottle was evacuated and flushed with $H_2$ styrene/ethylbenzene (by GC).

Other embodiments are within the claims. For example, glassy carbons containing metal particles other than platinum can be prepared by cross-linking and annealling complexes having formula 1, 2, 4, 5, 6 (M=Ni), 7 (M=Ni), 8, 9, and 10. Moreover, glassy carbons containing heteroatoms such as N can be prepared, for example, by cross-linking and annealling a complex having formulae 3.

Glassy carbons containing dispersions of metal particles can be prepared from acetylenic oligomers lacking aromatic groups, for example, some of the acetylenic oligomers described in Hay, U.S. Pat. No. 3,332,916, which is hereby incorporated by reference. In addition, the glassy carbons can be prepared from other, non-acetylenic precursors, such as phenolic formaldehyde oligomers, that are complexed to a metal.

What is claimed is:

1. A method of producing glassy carbon containing metal particles, comprising providing a metal complexed to a molecule which cross-links when heated to form a glassy carbon; and heating said metal complex for a period of time for said molecule to cross-link to form glassy carbon containing metal particles.

2. The method of claim 1, wherein said molecule includes an acetylene group.

3. The method of claim 1, wherein said metal complex cross-links to provide glassy carbon at a temperature of less than 1000° C.

4. The method of claim 3, wherein said metal complex cross-links to provide glassy carbon at a temperature of less than 750° C.

5. The method of claim 3, wherein said metal complex cross-links to provide glassy carbon at a temperature of less than 600° C.

6. The method of claim 1, wherein said molecule is a polymer including aromatic groups.

7. The method of claim 1, wherein said metal is a transition metal.

8. A method comprising providing a metal complexed to a molecule which cross-links when heated to form glassy carbon;

cross-linking said molecule to form glassy carbon containing metal particles;

incorporating said glassy carbon into an electrode; and incorporating said electrode into an electrochemical cell.

9. The method of claim 8 wherein said cross-linking comprises heating said molecule.

10. The method of claim 8 wherein said metal particles have an average size of less than 1 micron.

11. The method of claim 8 wherein said molecule includes an acetylene group.

12. A method of producing glassy carbon including a dispersion of metal particles, comprising providing a metal complexed to a molecule which cross-links when heated to form glassy carbon; and cross-linking said molecule to provide glassy carbon including a dispersion of particles of said metal.

13. The method of claim 12, wherein said molecule includes an acetylene group.

14. The method of claim 12, wherein said metal has a particle size of less than 100 nanometers.

15. A method comprising providing glassy carbon including within said glassy carbon a dispersion of metal particles having a size of less than 10 nanometers;

incorporating said glassy carbon into an electrode; and incorporating said electrode into an electrochemical cell.

16. The method of claim 15, further comprising using said electrochemical cell as a fuel cell.

17. The method of claim 15, further comprising using said electrochemical cell for electrochemical synthesis.

18. The method of claim 15, further comprising using said electrochemical cell as a sensor.

19. A method of producing a cross-linked carbon matrix including metal particles, comprising providing a metal complexed to a molecule which cross-links when heated to form an $sp^2$-hybridized carbon matrix; and cross-linking said molecule sufficiently to form an $sp^2$ hybridized carbon matrix having microcrystalline graphite domains having lattice dimension of between 1 nanometer and 20 nanometers.

20. The method of claim 19, wherein said lattice dimensions are between 2.5 nanometers and 7.5 nanometers.

21. A method of producing a cross-linked, conductive carbon matrix, comprising, providing a metal complexed to a molecule which cross-links when heated to form a conductive $sp^2$-hybridized carbon matrix; and cross-linking said molecule sufficiently to form an $sp^2$-hybridized carbon matrix having a conductivity of at least 0.01 s/cm.

* * * * *